United States Patent
Detsch

[19]

[11] Patent Number: 5,830,225
[45] Date of Patent: Nov. 3, 1998

[54] DENTAL AND MEDICAL TISSUE KNIFE

[76] Inventor: Steven G. Detsch, 4115 The Hill Rd., Bonita, Calif. 92002

[21] Appl. No.: 699,350

[22] Filed: Aug. 19, 1996

[51] Int. Cl.$^6$ .................................................. A61B 17/32
[52] U.S. Cl. ............................................ 606/167; 606/183
[58] Field of Search .................................. 606/167, 170, 606/183, 160, 166; 30/173, 121, 304, 113.1

[56] References Cited

U.S. PATENT DOCUMENTS

| | | | |
|---|---|---|---|
| 3,998,229 | 12/1976 | Barton | 30/121 X |
| 4,026,295 | 5/1977 | Lieberman | 30/294 X |
| 4,239,045 | 12/1980 | Schlein | 606/167 X |
| 4,365,957 | 12/1982 | Das | 433/144 |
| 5,026,385 | 6/1991 | Schutte et al. | 606/167 |
| 5,217,476 | 6/1993 | Wishinsky | 606/167 |
| 5,411,510 | 5/1995 | Fugo | 606/166 |
| 5,447,516 | 9/1995 | Gardner | 606/167 |

*Primary Examiner*—Michael Powell Buiz
*Assistant Examiner*—Nancy Mulcare
*Attorney, Agent, or Firm*—Michael W. York

[57] ABSTRACT

A manual dental and medical living tissue cutting instrument for obtaining living tissue grafts. The manual dental and medical tissue cutting instrument includes an elongated member with two portions. One portion is sized and shaped to be grasped by the hand of the user of the cutting instrument and the other adjacent blade holding portion that is located at the end of the elongated member and is adapted to hold two removable blades. The blade holding portion is adapted to hold the two removable blades in an angular relationship with each other in such a manner that the pointed ends of the removable blades either touch or come in close proximity to each other. The invention includes both the elongated member with its handle portion and blade holding portion without the removable blades and the combination of the elongated member and the removable blades.

3 Claims, 3 Drawing Sheets

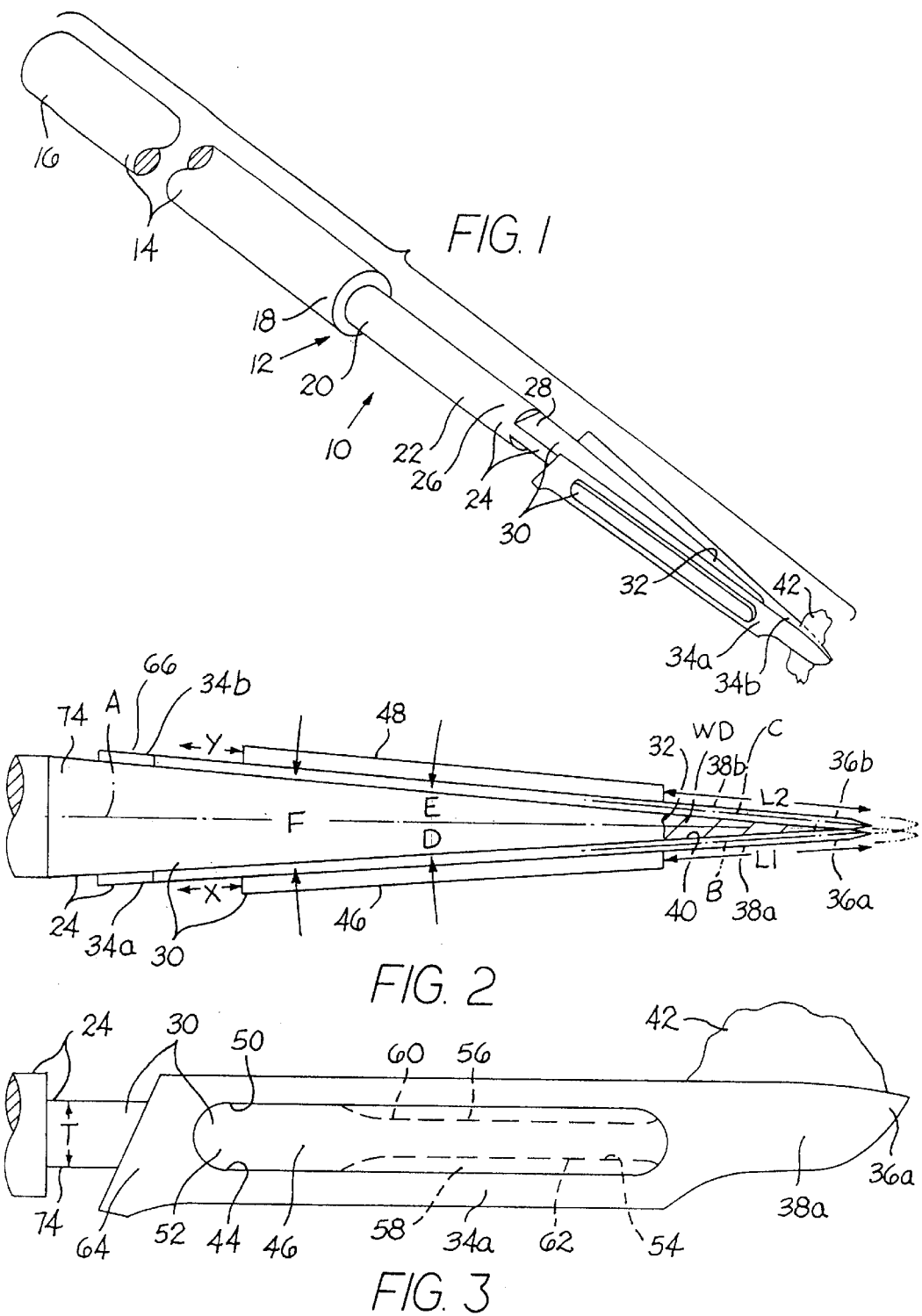

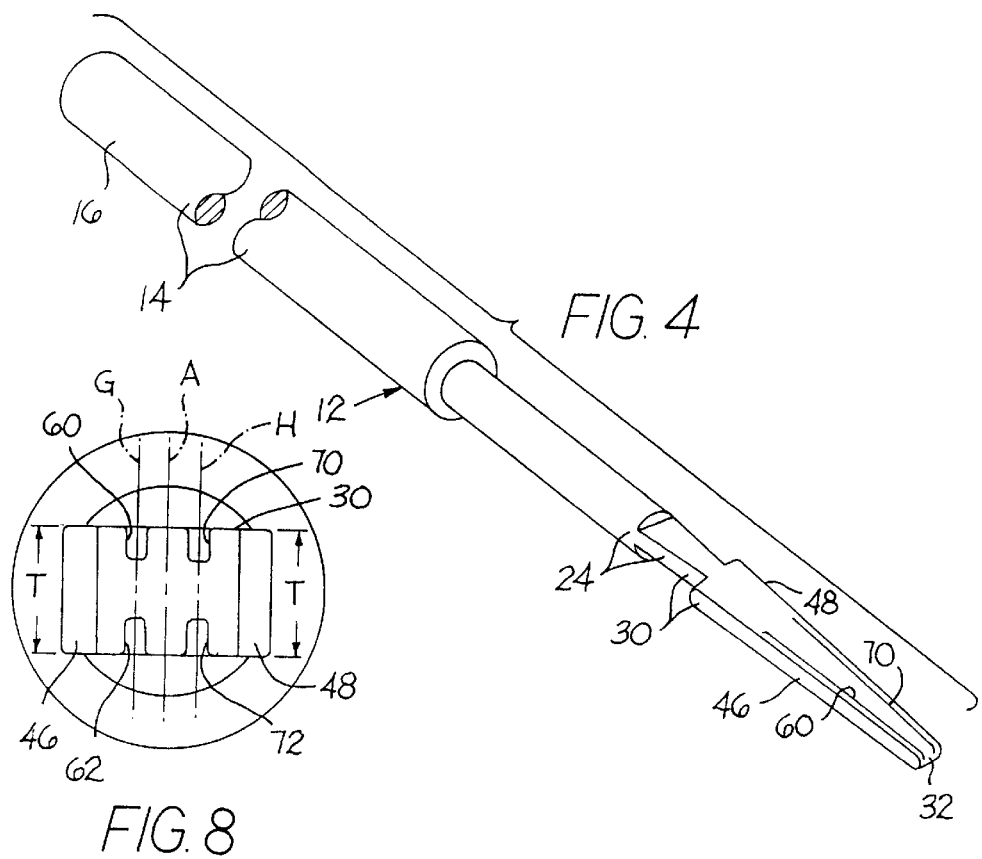
FIG. 4
FIG. 8
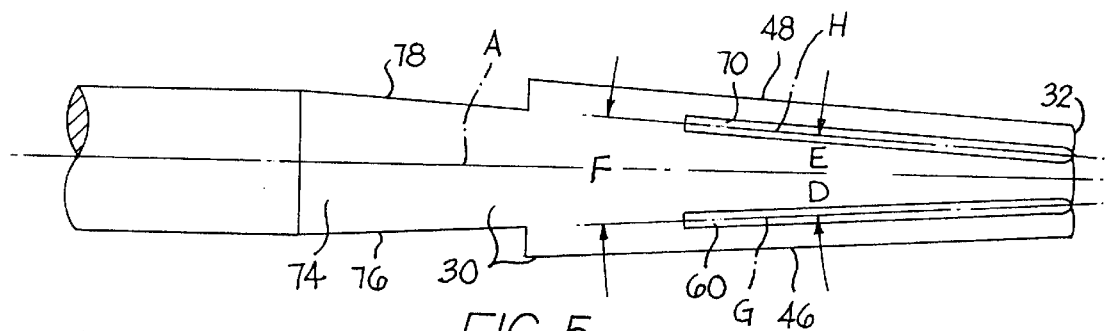
FIG. 5
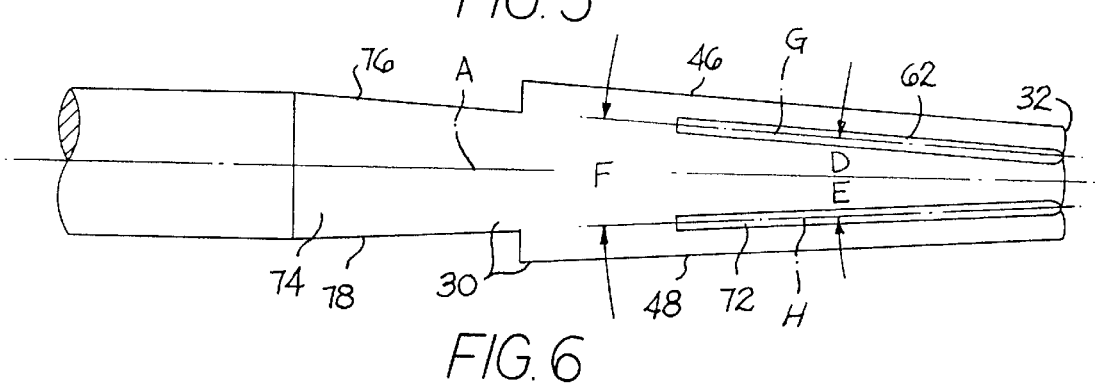
FIG. 6

DENTAL AND MEDICAL TISSUE KNIFE

BACKGROUND OF THE INVENTION

It is well recognized that living tissue is very important for transplantation in a variety of portions of a human body. With respect to living tissue in the mouth, it has been determined that deficient or defective gingival tissue can be replaced by tissue grafts that are taken from the mouth of the patient.

Connective tissue graft root coverage has proven to be a predictable and reliable means of correcting gingival recession and other gingival esthetic problems. However, obtaining uniform grafts in the mouth and elsewhere has not been easy. In this connection, secondary and tertiary incisions and subsequent dissection have been previously necessary with obtaining connective tissue in the mouth.

There have been numerous cutting instruments that have been proposed for both dental and non-dental and medical and non-medical uses. An early example of such an instrument is presented in U.S. Pat. No. 435,632. However, the cutting instrument is not suitable for practical medical or dental cutting use.

Other U.S. Pat. Nos. 3,688,407; 3,934,591 and 4,038,986 do disclose cutting instruments that are suitable for general dental or medical use. However, none of the inventions disclosed in these patents enable the easy cutting of tissue of a precise width and depth without a great deal of skill on the part of the user of the instrument. Also, such instruments require that the user make at least two cuts to get a segment of graft tissue. In addition, a high degree of skill is required to obtain a tissue graft that has a useable thickness for grafting.

This invention uses two disposable blades to overcome the previous problems associated with medical and dental cutting instruments. While there have been knives with two blades such as those presented in U.S. Pat. Nos. 1,226,797; 2,528,166 and 4,574,431 these are designed for cutting fruit or fish or the like and are not suitable for medical or dental graft tissue use.

This invention provides a simple dental and medical tissue cutting knife instrument that eliminates or greatly reduces the problems associated with the other cutting instruments set forth above. Moreover, the dental and medical tissue cutting knife instrument described herein is particularly useful for rapidly obtaining tissue that can be used for tissue grafting and the like. This dental and medical tissue cutting tissue knife eliminates the need for secondary and tertiary incisions. With this dental and medical tissue knife, the knife is drawn through the tissue and the released tissue issues out through the back of the knife through the two blades that are angled toward each other. In the knife's present configuration the connective tissue harvested measures 1.0 to 1.5 millimeters in thickness. Varying the tip width and angle of the disposable blade convergence will yield knife variations yielding tissue thickness of greater or lesser thickness than 1.0 to 1.5 millimeters. The width of the tissue harvested varies with the depth, the blades are inserted into the tissue. One centimeter to one and one-half centimeter wide grafts are routinely possible depending upon palatal configuration, once harvesting technique has been mastered. Mounting disposable blades of varying shapes and lengths improves access for harvesting tissue from difficult to reach areas such as the retromolar pad behind the molars.

SUMMARY OF THE INVENTION

This invention relates to dental and medical cutting instruments for cutting tissue and more particularly to dental and medical cutting instruments for cutting living tissue for tissue grafts.

It is an object of the present invention to provide a dental and medical tissue cutting knife instrument that is particularly useful in obtaining connective tissue and epidermal tissue grafting tissue.

It is an object of the present invention to provide a dental and medical tissue cutting knife instrument that is readily usable.

It is an object of the present invention to provide a dental and medical tissue cutting knife instrument that is readily reusable.

It is an object of the present invention to provide a dental and medical tissue cutting knife instrument which enables the easy procurement of tissue of a desired depth and width.

It is also an object of the present invention to provide a dental and medical tissue cutting knife instrument that is easy to sterilize.

It is also an object of the present invention to provide a dental and medical tissue cutting knife instrument which may be sterilized via usual procedures.

It is also an object of the present invention to provide a dental and medical tissue cutting knife instrument that can be readily used by one skilled in the art without any undue amount of special training.

It is also an object of the invention to provide a dental and medical tissue cutting knife instrument that uses blades that are easy to attach and detach.

It is also an object of the invention to provide a dental and medical tissue cutting knife instrument that uses two blades.

It is also an object of the invention to provide a dental and medical tissue cutting knife instrument that uses blades having a variety of shapes of cutting edges.

It is also an object of the invention to provide a dental and medical tissue cutting knife instrument in which the planes of the blades angle toward each other.

It is also an object of the invention to provide a dental and medical tissue cutting knife instrument in which the planes of the blades are at an angle so that the points of the blades angle toward each other.

It is also an object of the invention to provide a dental and medical tissue cutting knife instrument in which the planes of two blades each form an equal angle with a plane through the center of the blade holder.

It is also an object of the invention to provide a dental and medical tissue cutting knife instrument in which the points of the blades touch each other.

It is also an object of the invention to provide a dental and medical tissue cutting knife instrument that uses a combined handle and blade holder.

It is also an object of the invention to provide a dental and medical tissue cutting knife instrument that uses a combined handle and blade holder that is easy to manufacture.

It is also an object of the invention to provide a dental and medical tissue cutting knife instrument that uses a combined handle and blade holder that is inexpensive to manufacture.

It is also an object of the invention to provide a dental and medical medical tissue cutting knife instrument that uses a combined handle and blade holder that can be manufactured using standard techniques.

It is also an object of the invention to provide a dental and medical tissue cutting knife instrument that uses a combined handle and blade holder that can be manufactured using a variety of techniques.

The present invention provides a manual tissue cutting instrument comprising an elongated member having two end portions, with one of the end portions comprising a handle portion for being held by the hand of the user of the manual tissue cutting instrument and the other end portion of the elongated member comprising a blade holder portion for holding blades. The invention also includes a plurality of tissue cutting blades having portions thereof adapted to be connected to the blade holder portion of the elongated member for holding the blades at an angular relationship for cutting living tissue.

BRIEF DESCRIPTION OF THE DRAWINGS

The invention will be hereinafter more fully described with reference to the accompanying drawings in which:

FIG. 1 is a perspective view of the dental and medical tissue cutting instrument of the present invention with a portion broken away for ease of illustration;

FIG. 2 is a top plan view of a portion of the dental and medical tissue cutting instrument illustrated in FIG. 1;

FIG. 3 is a side elevational view of the dental and medical tissue cutting instrument illustrated in FIG. 2;

FIG. 4 is a perspective view of the dental and medical tissue cutting instrument illustrated in FIG. 1 without its cutting blades;

FIG. 5 is a top plan view of a portion of the dental and medical cutting instrument illustrated in FIG. 4;

FIG. 6 is a bottom plan view of the portion of the dental and medical cutting instrument illustrated in FIG. 5;

FIG. 8 is an end view of the dental and medical cutting instrument illustrated in FIG. 7 taken in the direction of the arrows 8—8 thereof.

DETAILED DESCRIPTION OF THE PREFERRED EMBODIMENT

Figure 7:
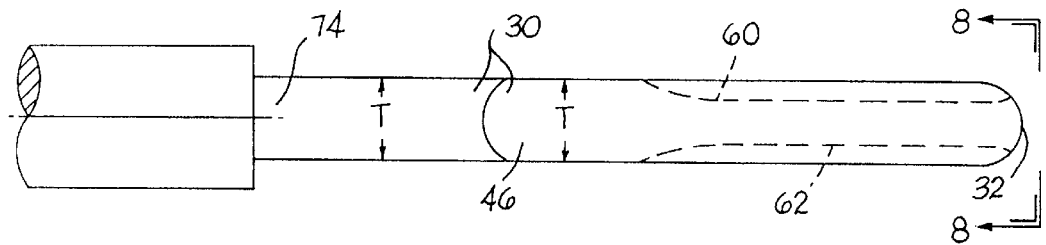
FIG. 7 is a side elevational view of the dental and medical cutting instrument illustrated in FIG. 5.

Referring first to FIG. 1, the dental and medical cutting instrument invention is illustrated and is designated generally by the number 10. The dental and medical cutting instrument comprises an elongated generally cylindrical shaped member designated by the number 12 that has a manual handle portion 14 whose outer end portion 16 also forms one end portion of the elongated member 12. The inner end portion 18 of the manual handle portion 14 is integrally connected to the inner end portion 20 of a substantially circular cross section cylindrical shank portion 22 that is part of a blade holder portion designated generally by the number 24. The outer end portion 26 of the shank portion 22 is in turn integrally connected to the inner end portion 28 of a blade connector portion 30. The outer end portion 32 of the blade connector portion 30 also forms the end portion for the elongated member 12 that is opposite its other end portion 16. As illustrated, the blade connector portion 30 secures two identical elongated substantially flat removable blades designated 34a and 34b and it can be readily seen that these blades are at an angular relationship with respect to each other.

FIGS. 2 and 3 that are respectively enlarged top plan and side elevational views of the outer portion of the blade holder portion 24 illustrated in FIG. 1 illustrate in greater detail the manner in which the removable blades 34a and 34b are connected to the blade connector portion 30 of the blade holder portion 24. As illustrated in FIG. 2, the blade holder portion 24 including its blade connector portion 30 has a center line plane designated by the letter A that extends lengthwise along the blade holder portion 24. In a similar manner the substantially flat identical blades 34a and 34b have respective center line planes designated by the letters B and C. These center line planes B and C form respective substantially equal angles D and E with the blade holder portion 24 center line plane A. The center line planes B and C of the respective blades 34a and 34b also form the angle F with respect to each other. The following relationships are also true:

$$\angle F = \angle D + \angle E$$
$$\angle F = 2 \angle D$$
$$\angle F = 2 \angle E$$
$$\text{Since} \quad \angle D = \angle E$$

It has been determined that the angle F should be between one (1) degree and twelve (12) degrees and in the preferred embodiment substantially six (6) degrees.

It will also be noted that the pointed end portions 36a and 36b of the respective blades 34a and 34b substantially come together to touch or substantially touch each other and this results in the adjacent cutting portions 38a and 38b of the blades 34a and 34b forming a substantially wedge shaped opening or aperture 40 through which tissue represented by the number 42, having an elongated wedge shaped cross section WD as illustrated in FIG. 2, passes as the blade portions 38a and 38b are drawn through living tissue as illustrated in FIGS. 1 and 3. This feature provides the dental and medical cutting instrument invention 10 with its unique living tissue harvesting capability for obtaining living tissue for use in tissue grafts of a particular desired cross section WD, which in this case is an elongated wedge shape whose edges form substantially an isosceles triangle.

To summarize the foregoing, it will be noted that the blade holder portion 24 for holding blades of the elongated member 12 has provisions for holding two substantially identical tissue cutting blades having portions thereof adapted to be connected to the blade holder portion 24 of the elongated member 12 with the blade holder portion being sized and shaped to hold the two blades, such as those designated 34a and 34b, with the center line planes B and C of the respective blades substantially opposite each other in an angular relationship. This angular relationship of the two oppositely located planes of the center lines of the blades, such as 34a and 34b, and the adjacent the blade holder portion 32 form an isosceles triangle for yielding a wedged shaped cross section tissue graft WD. As illustrated in FIG. 2, it should be noted that varying the angular relationship of the planes B and C of the center lines of the blades, such as the blades 34a and 34b, being held by the blade holder portion 24 will vary the thickness of the tissue graft cross section WD. It should also be noted that for a given blade center line plane angular relationship that the length of the cutting portion of the blades, such as that indicated in FIG. 2 by L1 and L2 for the respective blades 34a and 34b, being held by the blade holder portion 24 will vary the width of the tissue graft cross section WD.

FIGS. 2 and 3 also illustrate how the blades 34a and 34b are connected to the blade connector portion 30 of the blade holder portion 24. Each blade 34a and 34b has an aperture such as that designated 44 for the blade 34a. It will be noted that the blade connector portion 30 has two elongated oppositely located substantially identical protrusions 46 and 48. The rear or inner portion 50 of the aperture 44 is sized and shaped to receive the inner portion 52 of the protrusion 46 and the same is true for the blade 34b. However, the forward portion 54 of aperture 44 is narrower than the rear or inner portion 50 and the adjacent edges 56 and 58 of the forward portion 54 are sized and shaped to slide into corresponding slots 60 and 62 located in the protrusion 46. The same is true for the blade 34b and the protrusion 48 as will hereinafter be illustrated and described in further detail.

As a consequence, the blades 34a and 34b are connected to the blade connector portion 30 by inserting the edges 56 and 58 into the slots 60 and 62 and pushing the blade, such as the blade 34a, to the rear until the rear aperture portion 50 snaps over the rear portion 52 of the protrusion 46. The same is accomplished with the blade 34b and the protrusion 48. Removal of the blade, such as the blade 34a is accomplished by pulling or pushing outward on the rear blade portion 64 until the rear aperture portion 50 clears the rear of the protrusion 52 and by then pushing forward on the blade 34 so that its edge portions 56 and 58 slide out of the slots 58 and 60. As illustrated in FIG. 2, the other blade 34b with its rear blade portion 66 is removed in the same manner from the protrusion 48. This ability to remove and replace the blades 34a and 34b is indicated by the dashed lines in FIG. 2 and the double headed arrows X and Y that represent forward and backward movement for disconnecting and connecting the blades 34a and 34b to the blade connector portion 30.

FIGS. 4 through 8 illustrate the same dental and medical cutting instrument 10 and portions thereof illustrated previously in FIGS. 1 through 3, but without the removable blades 34a and 34b. Since the blades 34a and 34b have been removed in FIGS. 4 through 8 it is possible to see in better detail the novel structure that permits the planes of the blades 34a and 34b to be located in an angular relationship with respect to each other and have their outer end portions 36a and 36b come together.

In FIG. 4 the generally cylindrical shaped elongated member 12 is illustrated with its manual handle portion 14 and outer end portion 16 and its blade holder portion 24 with its blade connector portion 30 and outer end portion 32 and its elongated protrusions 46 and 48. The slot 60 for the portion 56 of the blade 34a is clearly visible in FIG. 4 as is an identical slot 70 for the corresponding portion of the blade 34b. Even in the perspective view set forth in FIG. 4 it is evident that the slots 60 and 70 taper toward each other as they progress or taper toward the end portion 32.

FIGS. 5 through 8 illustrate in detail the novel portions of the blade connector portion 30. These figures clearly indicate the slots 60 and 62 for portions of the blade 34a and the respective corresponding substantially identical slots 70 and 72 for portions of the blade 34b. In this connection it should be noted that FIGS. 5 and 6 are respective top and bottom plan views of the blade connector portion 30. As illustrated in FIGS. 5 and 6, the planes of respective slots 60 and 70 and 62 and 72 represented by the letters G and H make the same angle F with respect to each other as previously illustrated in and described with respect to FIG. 2 with respect to the planes of the blades 34a and 34b.

As indicated, these planes G and H make the angles D and E with respect to the center line plane A. As best illustrated in FIG. 8, the respective slots 60 and 62 and 70 and 72 are located opposite each other in the blade connector portion 30 and these slots 60 and 62 and 70 and 72 lie in the same respective planes represented by the letters G and H. In the preferred embodiment, the planes G and H each make an angle of three (3) degrees with the vertical plane A through the center of the blade connector portion 30. With this embodiment, the blades, such as those designated 34a and 34b or 80a and 80b, extend a distance of substantially 0.548 of an inch from the outer end portion 32 of the blade connector portion 30 to the point where the the points of the blades contact each other. Also in this preferred embodiment, the distance from the plane of the center line of the slot G or H is substantially 0.030 of an inch from the center line plane A when measured at the the outer end portion 32 of the blade connector portion 30.

As best illustrated in FIGS. 7 and 8, the elongated projections 46 and 48 have substantially the same thickness T as the adjacent tapered portion 74. In addition, as best illustrated in FIGS. 5 and 6, the tapered portion 74 has respective substantially flat tapering surfaces 76 and 78 and these surfaces 76 and 78 lie substantially in the respective planes G and H formed by the center lines of the respective slots 60 and 62 and 70 and 72. This location of the substantially flat surfaces 76 and 78 and the thickness T, as well as the location of the slots 60, 62 and 70 and 72, allows the respective blades 34a and 34b to be readily connected to the connector portion 30 and be readily secured in place on the connector portion 30 as well as to be readily removed from the connector portion 30. This is because the thickness T of the portion 74 is such that the rear portions 64 and 66 of the respective blades 34a and 34b extend above and below the tapered portion 74 so that outward and forward pressure can be exerted on the rear portions 64 and 66 to cause the rear portions 64 and 66 of the blades 34a and 34b to be slipped over the respective elongated protrusions 46 and 48 and the blades 34a and 34b to be pushed forward and out of the slots 60 and 62 and 70 and 72. This, of course, can be reversed to connect the blades or new blades 34a and 34b to the connector portion 30 by pushing the appropriate blade portions into the slots 60 and 62 and 70 and 72.

Figure 9:
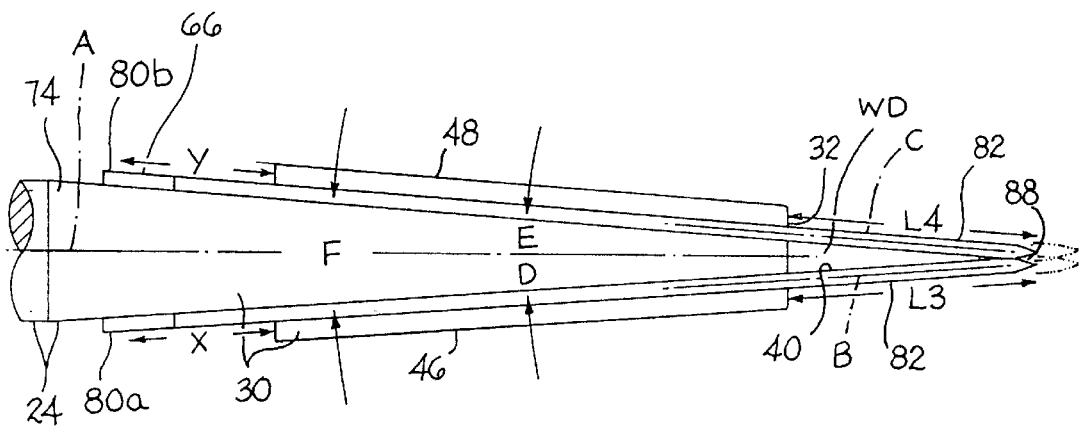
FIG. 9 is a top plan view of a portion of the dental and medical tissue cutting instrument substantially identical to that illustrated in FIG. 2 but illustrating a different blade pair embodiment.
Figure 10:
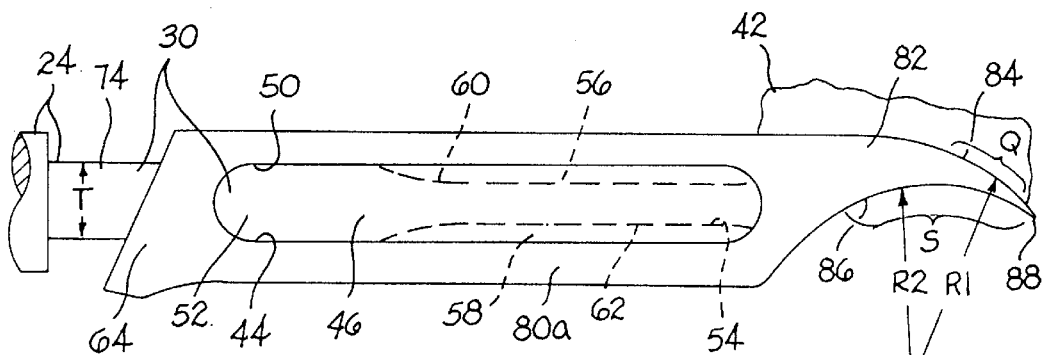
FIG. 10 is a side elevational view of the dental and medical tissue cutting instrument alternative blade pair embodiment illustrated in FIG. 9.

FIGS. 9 and 10 illustrate the previously described dental and medical cutting instrument 10, but with a different blade pair than set forth in FIGS. 1, 2 and 3. These alternative blades are designated 80a and 80b. The basic or non-cutting portions of the blades 80a and 80b are identical to the blades 34a and 34b and the blades 80a and 80b are removably connected to the blade connector portion 30 of the blade holder portion 24 in the same manner as the blades 34a and 34b. Each blade 80a and 80b has, the same as each blade 34a and 34b, an aperture such as that designated 44 for the blade 34a. As previously indicated, with respect to the blades 34a and 34b and the blade connector portion 30 with two elongated oppositely located substantially identical protrusions 46 and 48, each blade 80a and 80b, such as indicated for the blade 80a, has a rear or inner portion 50 of the aperture 44 of the blade 80a that is sized and shaped in the same manner as the blade 34a to receive the inner portion 52 of the protrusion 46. The same is true for the blade 80b as was previously indicated for the blade 34b. In the same manner as previously indicated for the blades 34a and 34b, the blades 80a and 80b also have, the forward portion 54 of the aperture 44 that is narrower than the rear or inner portion 50 and the adjacent edges 56 and 58 of the forward portion 54 are sized and shaped to slide into corresponding slots 60 and 62 located in the protrusion 46.

As a consequence, the blades 80a and 80b, as previously indicated for the blades 34a and 34b, are connected to the blade connector portion 30 by inserting the edges 56 and 58 into the slots 60 and 62 and pushing the blade, such as the blade 80a to the rear until the rear aperture portion 50 snaps over the rear portion 52 of the protrusion 46. The same is accomplished with the blade 80b. Removal of the blade, such as the blade 80a is accomplished by pulling or pushing outward on the rear blade portion 64 until the rear aperture portion 50 clears the inner portion 52 of the protrusion 46 and by then pushing forward on the blade 80a so that its edge portions 56 and 58 slide out of the slots 60 and 62.

As illustrated in FIG. 9, the other blade 80b with its rear blade portion 66 is removed in the same manner as the blade 80a. This ability to remove and replace the blades 80a and 80b as previously indicated for the blades 34a and 34b is indicated by the dashed lines in FIG. 9 and the double headed arrows X and Y that represent forward and backward movement for disconnecting and connecting the blades 80a and 80b from or to the blade connector portion 30. The blades 80a and 80b are specifically configured for dental use.

As best illustrated in FIG. 10, each blade 80a and 80b that are identical as indicated for the identical blade 80a has an important cutting end portion designated generally by the number 82. This portion 82 is generally claw shaped as viewed from the side and has an outer curved edge 84 that can be non-cutting that can or a cutting edge and an inner curved cutting edge 86. As indicated both of these edges 84 and 86 come together at a point designated by the number 88. As indicated, both the curved edge 84 and the curved cutting edge 86 have portions substantially conforming to the outer circumference of a circle that are designated by the letters Q and S. The respective radii for these substantially circular portions are represented by R1 and R2 and in the preferred embodiment R1 and R2 have substantially the same center of rotation C. R.

From the foregoing it is apparent that the blade holder portion 24 is sized and shaped for removable blades having different configurations such as those represented by 34a and 80a. This fact that the manual living tissue cutting instrument's the blade holder portion 24 is sized and shaped for blades having different configurations provides the ability for the manual living tissue cutting instrument 10 with various shaped cutting portion blades, such as those designated 34a, 34b or 80a, 80b, to gain access to various possible tissue graft sites.

As indicated previously for the manual living tissue cutting instrument 10 with the blades 34a and 34b, it will also be noted in the same manner for the blades 80a and 80b that the blade holder portion 24 for holding blades of the elongated member has provisions for holding the two substantially identical tissue cutting blades 80a and 80b having portions thereof adapted to be connected to the blade holder portion 24 of the elongated member 12 with the blade holder portion being sized and shaped to hold the two blades 80a and 80b with the planes of the blades B and C substantially opposite each other in an angular relationship. As indicated previously, this angular relationship of the two oppositely located planes of the blades, now blades 80a and 80b, and the adjacent the blade holder portion 32 form an isosceles triangle for yielding a wedged shaped cross section tissue graft WD in FIG. 9. It should be noted that varying the angular relationship of the planes of the blades, such as blades 80a and 80b, being held by the blade holder portion will vary the thickness of the tissue graft cross section designated WD in FIG. 9. It will also be noted that for a given blade center line plane angular relationship that the length of the cutting portions blades, such as that indicated in FIG. 9 by L3 and L4 for the respective blades 80a and 80b, being held by the blade holder portion 24 will vary the width of the tissue graft cross section WD as set forth in FIG. 9.

The dental and medical cutting instrument invention 10 is made and used in the following manner. The elongated generally cylindrical member 12 is formed from surgical grade stainless steel using forging techniques known in the art. Then the elongated member 12 is suitable machined using conventional machining equipment known in the art. The individual blades 34a and 34b are in themselves readily formed by means known in the art. However, the blades 80a and 80b are specifically configured with the cutting edges for dental use.

The dental and medical cutting instrument invention 10 is normally used in the following manner. The elongated member 12 is normally supplied separately packaged from the blades such as the blades 34a and 34b or 80a and 80b. After the elongated member 12 is unpackaged, it would normally be sterilized using conventional sterilization methods. The blades, such as the blades 34a and 34b or 80a and 80b would normally be received in sterile packages. These blades 34a and 34b or 80a and 80b would then be manually connected to the blade connector portion 30 of the blade holder portion 24 of the elongated member 12.

To accomplish the task of connection of the blades 34a and 34b or 80a and 80b to the blade connector portion 30, the blades 34a and 34b or 80a and 80b are positioned in such a manner that appropriate portions of these blades 34a and 34b or 80a and 80b engage the forward portions of the respective slots 60 and 62 and 70 and 72. The blades 34a and 34b or 80a and 80b are then pushed or pulled to the rear or toward the manual handle portion 14 until the rear portions 64 and 66 with their associated rear aperture portions, such as the rear aperture portion 50 for the blade 34a, snap or fit over the respective rear portions of the elongated projections 46 and 48 in the manner illustrated in FIGS. 3 and 10 for the rear portion 52 of the protrusion 46.

In this connection, the location of the substantially flat surfaces 76 and 78 and the thickness T, as well as the location of the slots 60, 62 and 70 and 72, allows the respective blades 34a and 34b or 80a and 80b to be readily connected to the connector portion 30 and be readily secured in place on the connector portion 30 as well as to be readily removed from the connector portion 30 since due to the thickness T of the portion 74, the rear portions 64 and 66 of the respective blades 34a and 34b or 80a and 80b extend above and below the tapered portion 74 so that outward and forward pressure can be exerted on the rear portions 64 and 66 to cause the rear portions 64 and 66 of the blades 34a and 34b or 80a and 80b to be slipped over the respective elongated protrusions 46 and 48 and the blades 34a and 34b or 80a and 80b to be pushed forward and out of the slots 60 and 62 and 70 and 72.

As set forth below, the use of the dental and medical cutting instrument 10 will be related to dental use, but it should be noted that equivalent procedures would be followed in medical uses. After mounting the opposed scalpel blades 34a and 34b or 80a and 80b on the blade connector portion 30 of the blade holder portion 24 of the cutting instrument 10, a palatal donor site is examined. The two prime donor areas are the retromolar tuberosity and palatal tissue adjacent to the second molar and the area from the mesial line angle of the maxillary first molar to the cuspid. The palatal area adjacent to the maxillary first molar while a source of connective tissue will often have exostosis as well as the nerve and blood vessel issuance of the palatal foremen. Removal of connective tissue from this area can lead to varying paresthesia and/or a bleeding episode. Angulation of the palate and depth of tissue to bone will effect a surgeon's ability to harvest tissue.

The blades, such as the blades 34a and 34b or 80a and 80b, are inserted into the tissue and the blades are drawn through the palatal tissue with a slight sawing motion. The released connective tissue, such as the tissue 42, will be noted exiting through the blades 34a and 34b and 80a and 80b as illustrated in FIGS. 1, 3 and 10. When a suitable length of graft has been achieved, the blades 34a and 34b or 80a and 80b are withdrawn from the palate. The connective tissue graft 42 should be tugged lightly to see if it is completely free from the surrounding donor area. If not, minimal dissection at the mesial and distal aspects of the incision usually completes the graft's removal. The graft should be kept moist until use. The incision edges while relatively narrow should be approximated and sutured to speed healing and for patient comfort. The blades 34a and 34b or 80a and 80b are removed after use and disposed of per normal protocols. It is strongly advised that new blades be used for each use and that no coagulated blood be on the blades before harvesting as the blood will restrict tissue passage through the blades.

Although the invention has been described in considerable detail with reference to certain preferred embodiments, it will be appreciated and understood that various changes and modifications may be made without departing from the spirit and scope of the invention as defined in the appended claims.

What is claimed is:

1. A manual living tissue graft cutting instrument for obtaining a living tissue graft comprising: an elongated member having two end portions with a portion thereof sized and shaped to be held by the hand of the user of said manual living tissue cutting instrument; one end portion of said elongated member having blade connecting means for connecting two blades to said one end portion of said elongated member; two substantially identical elongated substantially flat tissue cutting blades each having an inner portion thereof secured to said blade connecting means and each having an outer portion thereof having a point, said blades being connected by said blade connecting means in side-by-side positions with the points of said blades angled toward each other.

2. The manual living tissue cutting instrument of claim 1 wherein said connecting means comprises means for permitting said blades to be removed from said blade connecting means.

3. The manual living tissue cutting instrument of claim 2 wherein said means for permitting said blades to be removed from said blade connecting means includes tapering slots holding portions of said blades.

\* \* \* \* \*